(12) United States Patent
So et al.

(10) Patent No.: US 8,531,659 B2
(45) Date of Patent: Sep. 10, 2013

(54) MULTIPASS CELL USING SPHERICAL MIRRORS WHILE ACHIEVING DENSE SPOT PATTERNS

(75) Inventors: Stephen So, Fairless Hills, PA (US); David Thomazy, Highland Park, NJ (US)

(73) Assignee: The Laser Sensing Company, Plainsboro, NJ (US)

( * ) Notice: Subject to any disclaimer, the term of this patent is extended or adjusted under 35 U.S.C. 154(b) by 0 days.

(21) Appl. No.: 13/426,683

(22) Filed: Mar. 22, 2012

(65) Prior Publication Data

US 2012/0242989 A1    Sep. 27, 2012

Related U.S. Application Data

(60) Provisional application No. 61/467,171, filed on Mar. 24, 2011.

(51) Int. Cl.
*G01N 1/10*    (2006.01)

(52) U.S. Cl.
USPC ........................................................ 356/246

(58) Field of Classification Search
USPC ........................................................ 356/246
See application file for complete search history.

(56) References Cited

U.S. PATENT DOCUMENTS

| | | | |
|---|---|---|---|
| 5,313,568 A | 5/1994 | Wallace et al. | |
| 6,370,178 B1 | 4/2002 | Papayoanou et al. | |
| 7,352,463 B2 | 4/2008 | Bounaix | |
| 7,477,377 B2 | 1/2009 | Silver | |
| 7,800,751 B1 | 9/2010 | Silver et al. | |
| 7,876,443 B2 | 1/2011 | Bernacki | |
| 2006/0158644 A1 | 7/2006 | Silver | |
| 2006/0232772 A1* | 10/2006 | Silver | 356/246 |
| 2008/0212217 A1 | 9/2008 | Robert | |

OTHER PUBLICATIONS

Silver, "Simple Dense-Pattern Optical Multipass Cells", Nov. 1, 2005/ vol. 44, No. 31/ Applied Optics, pp. 6545-6556.
Fuβ et al, "IR Multiphoton absorption and isotopically selective dissociation of CHClF2 in a Herriott Multipass Cell", Z. Phys. D 29, 291-298 (1994).
Robert, "Simple, stable, and compact multiple-reflection optical cell for very long optical paths", Applied Optics/ vol. 46, No. 22/ Aug. 1, 2007, pp. 5408-5418.
Bartlome et al., "High-temperature multipass cell for infrared spectroscopy of heated gases and vapors", 2007 American Institute of Physics, pp. 013110-1/013110-6.
Berezin et al., "Exact Solution for Chernin four objective multipass cell", Natural Sciences Center of General Physics.

* cited by examiner

*Primary Examiner* — Tu Nguyen
(74) *Attorney, Agent, or Firm* — Wendy W. Koba

(57) ABSTRACT

A technique for designing a multipass optical cell utilizes an iterative artificial intelligence-based optimization process based upon evaluation of direct ray tracing with mirrors simulated as having true spherical surfaces (i.e., defined as a "thick lens") to identify particular cell configurations that result in creating spot patterns which fill a significant portion of the surface of each mirror without significant spot overlap. This technique allows the use of relatively simple, low-cost spherical mirrors while providing the desired dense spot patterns.

26 Claims, 3 Drawing Sheets

US 8,531,659 B2

MULTIPASS CELL USING SPHERICAL MIRRORS WHILE ACHIEVING DENSE SPOT PATTERNS

CROSS-REFERENCE TO RELATED APPLICATIONS

This application claims the benefit of U.S. Provisional Application No. 61/467,171, filed Mar. 24, 2011 and herein incorporated by reference.

TECHNICAL FIELD

The present invention relates to an optical multipass cell (MPC) configuration and, more particularly, to an arrangement that is configured using direct ray tracing techniques to create spot patterns that fill a significant portion of the surface of each mirror without significant beam spot overlap.

BACKGROUND OF THE INVENTION

A known and successful system for detecting small quantities of gas in the environment is by the use of absorption spectroscopy. By this technique, a light beam of selected wavelengths that are highly absorbed by the particular gas for which the instrumentation is designed to detect passes through a sample of the gas. The rate of absorption of the light beam is used as an indicator of the level of concentration of the gas in the same. In order to improve the sensitivity of detecting low levels of concentration of gas by spectral absorption, it is necessary to pass the light beam through a relatively long pathway of the gas sample. Stated another way, as the length of the light beam passing through a sample is increased, the sensitivity of the instrument to detect very small levels of gasses is also increased, since the absorption increases.

It is easy to understand that if a beam is passed through a very long tube containing a sample of gas that the instruments requiring such a long tube would be extremely cumbersome and therefore not easily portable. To overcome this problem, others have devised systems wherein a beam of light is repeatedly reflected between opposed mirrors to thereby extending the length of exposure of the beam to a gas sample in a way that the size of the instrument can be substantially reduced.

A typical absorption cell of this type is referred to as a "multipass cell" and comprises an elongated cylinder in which mirrors are disposed at opposite ends and light is introduced into the cells through a hole in one of the mirrors. These multipass cells necessarily avoid having the mirror bounce spot locations overlap, since scattered light from each spot can reflect into the overlapped spot's beam direction, causing an interference etalon fringe pattern. These cells also generally use concave mirror surfaces to refocus the beam on each bounce, preventing the laser beam from diverging over the long optical path.

FIG. 1 illustrates an exemplary prior art multipass cell arrangement 1, comprising a pair of mirrors 2, 3 which are separated by a predetermined spacing d to form an optical cavity. Mirrors 2, 3 each have the same radius of curvature in this example, and take the form of spherical mirrors with a point focus. In order to create a spot pattern, an incoming laser beam is introduced into the cavity at an off-axis orientation (i.e., off-axis with respect to the optical axis OA of arrangement 1). Referring to FIG. 1, an incoming laser beam I is shown as being provided by a laser source 5 and introduced in the system through a hole 4 formed in mirror 3. Incoming laser beam I then bounces multiple times between mirrors 2 and 3, ultimately exiting through hole 4, as shown, and entering a detector 6. This particular prior art embodiment is described as a "reentrant" configuration, since the output laser beam passes through the same aperture as the input beam.

An exemplary spot pattern formed by the bounces is also shown in FIG. 1. Obviously, by increasing the number of bounces (thus, the number of spots), the optical path length increases. For many arrangements, such as in trace gas sensing as noted above, it is preferred to utilize a relatively long optical path length (measured in meters, at times tens of meters) within a relatively small physical size (that is, a separation d which tends to be more on the order of centimeters). While increasing the spot density provides this desired result, it is also important to prevent overlap of the spots (which otherwise creates unwanted interference effects, fringe patterns and the like). Inasmuch as the prior art configurations typically utilize spherical members which create spot patterns that are either a single circular or single elliptical pattern in form, these cells are limited in the number of spots that can be formed before overlapping occurs.

There are various multipass cell configurations known in the art which do not overlap spots in a relatively dense pattern. These configurations generally take the form of either pure astigmatic cells or cylindrical mirror-based multipass cells, rather than using the conventional spherical mirrors. The mirrors for pure astigmatic cells must be machined to extremely high tolerances to achieve the correct amount of astigmatism (thereby increasing overall system cost), and mismatched mirrors require rotation of one of the mirrors to provide the desired reentrant condition (i.e., matching of input and output beam locations for maximum stability, as described in U.S. Pat. No. 5,291,265, discussed below). The astigmatic cell was first described in the article "Off-axis paths in spherical mirror interferometers" by D. Herriott et al., appearing in *Applied Optics*, Vol. 3, page 523 et seq., 1964. A significant problem with the use of the astigmatic configuration is the high cost of extreme-precision tolerance mirrors with exact focal lengths to achieve a stable, predictable reentrant pattern. An alternative to the precision tolerance ground mirrors is to use a spherical mirror with compressing stress along one axis to bend the mirror and achieve an astigmatic mirror; however, this is not a stable configuration. Improvements to the development of such cells using relaxed tolerance astigmatic mirrors have been developed by Aerodyne Research, Inc., as disclosed in U.S. Pat. No. 5,291,265 issued to P. L. Kebabian on Mar. 1, 1994, which utilizes a pair of mirrors that are fabricated so that the ratios of their radii of curvature are actually larger than the values calculated from simulations. This improvement allows for the rotation of the mirrors about their axes to achieve the reentrant condition, enabling the use of lower tolerance mirrors. These cells produce a Lissajous pattern that only fill a diamond-shaped area on the mirror, wasting space around the periphery of the circular mirrors.

The cylindrical mirror-based multipass cells (where at least one mirror is cylindrical) provide the same astigmatic configuration of spots and are lower cost. However, the cylindrical patterns do not refocus the beam in both vertical and horizontal directions for each mirror bounce and, therefore, are more difficult to align and achieve the pattern density required for very high bounce number applications. A recent type of astigmatic cell using cylindrical mirrors is described in U.S. Pat. No. 7,307,716 entitled "Near Reentrant Dense Pattern Optical Multipass Cell" and issued to J. A. Silver on Dec. 11, 2007. Cylindrical mirrors are typically ground with a poorer precision surface quality ($\lambda$), which can cause scattering of the optical beam, leading to increased fringing when compared to off-the-shelf spherical mirrors that are ground at better than $\lambda/4$, and frequently $\lambda/8$. As with the above-cited Kebabian configuration, this cylindrical-based design also produces a Lissajous pattern (which wastes space on the mirror surface).

One of the newer types of multipass cell utilizes a specially-designed spherical mirror-based arrangement, utilizing a "split spherical mirror" as one termination, as described in the article "Simple, stable and compact multiple-reflection optical cell for very long optical paths" by C. Robert and appearing in *Applied Optics*, Vol. 46, No. 22, August 2007, p. 5408 et seq. While providing an increase in spot density (and, as a result, optical path length), this type of cell causes the spot pattern to spiral into the center and presents some beam quality issues, since the beam traversing the spot pattern does not reflect on symmetric surfaces, causing major skew of the beam in one direction. When the beam is skewed in this manner with no counter-acting effects, it is more difficult to create high numbers of spots on a mirror.

A majority of these and other prior art arrangements implement matrix ray tracing techniques to simulate the spot pattern before implementation. Commonly, a standard ABCD matrix with thin lens paraxial approximation allows fast simulation, showing a good approximation of the spot positions of standard spherical Herriott calls, especially those with all spots in the same approximate z-plane on a mirror (for example, a single circle spot pattern). More complicated tracers have been developed that use an ABCDEF matrix to account for displaced and tilted surfaces, but preserve paraxial and thin lens approximations.

By continuing to rely on these approximations, however, the various prior art techniques introduce considerable errors into the ray tracing results, particularly after long paths and multiple reflections. For example, at an angle of 5°, the paraxial approximation of $\theta \approx \sin\theta$ is in error by 0.1%, where these errors are not accounted for in these matrix-based calculations.

SUMMARY OF THE INVENTION

The needs remaining in the art are addressed by the present invention, which relates to an optical multipass cell (MPC) configuration and, more particularly, to a novel technique for designing an MPC that does not utilize the thin lens and paraxial approximations. Instead, the present invention utilizes an iterative artificial intelligence-based optimization via direct ray tracing with mirrors simulated as having true spherical surfaces (i.e., defined as a "thick lens") to identify particular cell configurations that result in creating spot patterns which fill a significant portion of the surface of each mirror without spots significantly overlapping (hereinafter referred to as "intricate, non-overlapping spot patterns", or simply "intricate" for the sake of discussion). As will be evident from the following discussion, the various configurations of the present invention produce dense spot patterns that are circular in shape, as opposed to the diamond-shaped patters associated with astigmatic and cylindrical cells, filling the entire circular mirror with spots.

In accordance with the present invention, an incoming laser beam is simulated as a set of rays (disposed in a geometrical pattern to define the beam width boundaries), and each ray is independently traced in three dimensions (vectors) as it passes between the pair of mirrors. Iterative computer simulations based on this vector-based ray tracer are used to create novel intricate spot patterns. Various factors are manipulated (either singly, or in combination with other parameters) to create these new, intricate spot patterns that fill a significant portion of the mirror surface without significant overlap. In particular, artificial intelligence (AI) genetic algorithms are used to select and test various combinations of parameters to identify those arrangements that create the desired high density, intricate spot patterns. This process performs an informed Monte Carlo optimization type of analysis that goes through different levels of maximizing aspects of the different components of the multipass cell configuration. Various parameters are used as "genes", and various mixing of different random combinations yields different levels of fitness, where the strongest combinations survive for the next iteration.

In accordance with the present invention, a set of input parameters that may be modified during the process of searching for an acceptable solution include the following: the location $(x_0, y_0)$ of the input laser beam at the mirror's surface (the entrance hole on a mirror); the orientation angle $\theta_x, \theta_y$ of this input beam with respect to the optical axis of the system; the distance d separating the opposing mirrors forming the cell; and the number of passes N that the beam makes before it exits the cell.

While an important design goal is to achieve a dense spot pattern (i.e., minimizing the separation between adjacent spots), other criteria that may be considered when evaluating specific arrangements include one or more of the following: ensuring that the rays remain "within bounds" of the surface of the spherical mirror; creating a sufficiently long optical path length; location of the exit hole with respect to the entrance hole; and location of the exit hole with respect to the "last" spot's neighboring spots (ensuring that the physical process of forming a hole of sufficient size for the exit beam doesn't come too near another spot on the mirror).

It is an advantage of the arrangement of the present invention that simple plano-concave spherical glass substrates can be used as the mirrors, providing a significant savings in fabrication expenses with respect to prior art dense spot pattern configurations that required the use of specially-designed astigmatic mirrors, cylindrical mirrors, split mirrors and the like. It is to be understood, however, that the direct ray tracing iterative optimization method of the present invention may also be used with these other mirror designs, if desired, to decrease wasted mirror surface area.

In one exemplary embodiment, the present invention comprises a multipass optical cell including a first mirror element forming a first end termination of the multipass optical cell and including an entrance hole forming an inlet for an incoming light beam and a second mirror element forming a second end termination of the multipass optical cell, the second mirror element disposed with respect to the first mirror element so that an incoming light beam will reflect multiple times between the first mirror element and the second mirror element, creating a spot pattern of locations where the beam impinges the reflecting surface of the first and second mirror elements, wherein one or more cell parameters are configured using an interactive artificial intelligence-based optimization via direct tracing of a plurality of separate rays forming the incoming light beam, utilizing actual curvature values of the first and second minor elements to create an intricate, dense spot pattern.

In another embodiment, the present invention discloses a method of creating a dense spot pattern within a multipass optical cell including the steps of: a) positioning a first mirror element as a first end termination of the multipass optical cell, the first mirror element having a first, defined curvature, b) positioning a second mirror element as a second end termination of the multipass optical cell, the second mirror element having a second, defined curvature, wherein the first and second mirror elements are separated by a distance d; c) defining an input beam as a plurality of separate rays; d) tracing the reflections of each separate ray as it interacts with the first and second mirror elements as a function of the actual curvatures of the first and second mirror elements and e) using artificial intelligence optimization to simulate varying one or more of: the location of the entrance hole on the first mirror element, the orientation of the incoming beam with respect to an optical axis of the first mirror element, the separation distance between the first mirror element and the second mirror element, the location of an exit hole on either one of the first and second mirror elements to create a dense spot pattern. In this method embodiment it is also possible optimize the shape of an incoming beam to create an output beam of a predetermined shape (such as a spherical output beam, for example).

In other alternative embodiments, the technique of the present invention can be used with multipass cell configurations employing three or more mirrors, applying the same direct ray tracing iterative optimization techniques as each ray is individually traced in a path as it traverses the cell and interacts with each mirror. Additionally, multipass cell arrangements that utilize arrangements other than a hole in a mirror to inject a beam into a cell can utilize the techniques of the present invention (with an appropriate adjustment of the parameters that are optimized to find a suitable configuration).

Other and further aspects and advantages of the present invention will become apparent during the course of the following discussion and by reference to related drawings.

BRIEF DESCRIPTION OF THE DRAWINGS

Referring now to the drawings.

DETAILED DESCRIPTION

As described above, it has been found that the prior art matrix-based ray tracing methods can contain significant errors after long paths and multiple reflections as a result of using the paraxial and thin lens approximations, unless the spot pattern is bouncing off surfaces that have a very large radius of curvature. For example, at an angle of 5°, the paraxial approximation of θ≈sin θ is in error by 0.1%, where the more strongly curved surfaces produce even more oblique reflections. Some correction has been obtained in the past by direct ray tracing of the equation-based solution and adjusting the final configuration to match this more exact ray tracing. However, the paraxial and thin lens approximations are retained for this process as well. The presence of these approximations and lack of equation-based designs that match the actual cell designs is considered to have limited the ability to develop other spot patterns that may otherwise provide viable MPC arrangements. In particular, the lack of consideration of spherical aberration effects, which are not easily simulated in matrix-based approaches, is considered to be a major limitation of these design efforts.

The present invention introduces the use of a different technique, which has resulted in the identification of many different spot patterns that provide denser arrangements than previously thought possible (since previously the only configurations generally pursued with high spot density using spherical mirrors were circular or elliptical). In particular, three-dimensional vector ray tracing techniques are used in accordance with the present invention to directly calculate the path taken by rays forming an incoming laser beam as the rays interact with true spherical surfaces (thought of as a "thick lens"), in contrast to the thin lens approximation of the prior art.

Figure 1:
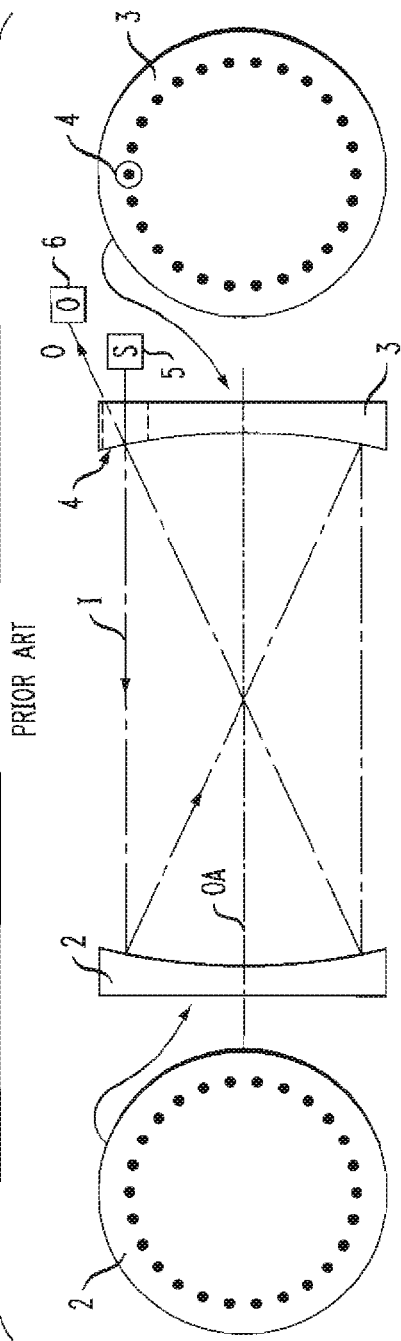
FIG. 1 is a diagram of an exemplary prior art multipass cell.
Figure 3:
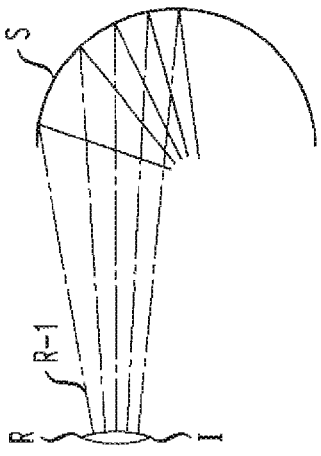
FIG. 3 illustrates the various paths following by the plurality of separate rays as they interact with a spherical surface.
Figure 2:
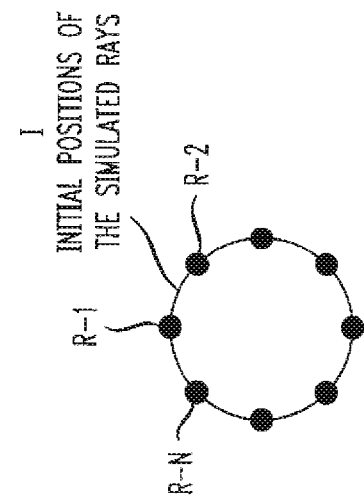
FIG. 2 depicts the simulation of a light beam as a plurality of separate rays disposed to outline the periphery of the light beam.

In particular, and as shown in FIG. 2, an incoming laser beam I is simulated by a plurality of rays R-1 through R-N, where the point origin of each ray R-i is initially placed on a circular outline I to define the beam shape of incoming laser beam I. FIG. 3 is a side view of this point origin of rays R and further shows the initial direction of rays R-1 through R-N toward a true spherical surface S. The curvature is exaggerated for the sake of illustration, but clearly illustrates the different paths taken by each ray. This shows that the "thin lens" approximation as used by the prior art, which ignores these different paths, misses important potential factors that impact the overall process of developing multipass cell designs. In contrast, therefore, the methodology of the present invention utilizes this true spherical design information to trace the progression of each individual ray as it bounces back and forth between a pair of spherical mirror surfaces, thereby defining a variety of different cell configurations that create dense, intricate spot patterns with little or no overlap.

Referring to FIGS. 2 and 3, the rays R have an initial direction which may be calculated by simulating an intricate beam parameter with a beam wavelength, and may exhibit a divergence equal to those of the specific laser used in the actual implementation. As shown in FIG. 3, the initial positions of each ray are traced along a three-dimensional vector path to its intersection with sphere S, and a bounce for each ray is calculated from the angle to the sphere. The tracing process is continued as the rays each bounce off of the opposing spherical mirror (not shown). The specific process uses line-sphere intersections to simulate the ray of light intersections and bouncing. While the exemplary arrangement shown in FIGS. 2 and 3 utilizes a plurality of rays disposed to define the periphery of the beam, it is to be understood that other geometries of ray locations may be used, as long as the periphery is well-defined. For example, additional rays may be positioned in the interior of the design and their paths traced using the same method. Indeed, it is further possible to use the techniques of the present invention to define an "optimized" shape of an input beam that will form a preferred geometry of the output beam (for example, to form a spherical output beam).

Instead of using the thin lens approximations of the prior art, the process of the present invention utilizes the actual spherical surface (i.e., a "thick lens"), where by searching through all of the various parameters than can be adjusted e.g., (location of entrance hole ($x_0$, $y_0$) on a first mirror, off-axis orientation of the incoming beam, separation between mirrors, desired number of passes N, diameter of the spherical mirrors and their focal length f), a variety of different spot patterns have been found that substantially increase the fill factor when compared to conventional spherical mirror-based multipass cells of the prior art.

In particular, a fitness function can be utilized to determine an acceptable MPC design, which can then be iterated with respect to the various parameters defined above. One acceptable fitness function takes the following form:

$$(N*d)^2 + id^2 + hd^2,$$

where d is the distance between the mirrors, N is the number of passes, id is the minimum inter-spot separation and hd is the minimum separation between a spot and either one of the entrance or exit holes. Solutions that create rays which exceed the "bounds" of the mirrors' surface (mirror clear aperture) are ignored, and can be set to zero or negative fitness.

Figure 4:
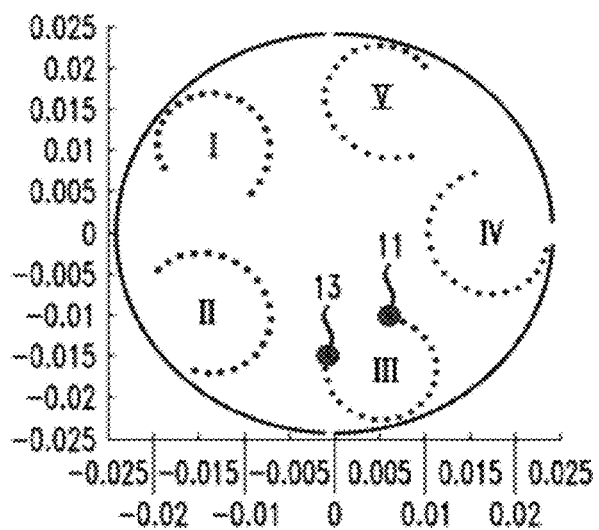
FIG. 4 illustrates an exemplary spot pattern that was developed using the direct ray tracing process of the present invention.

FIG. 4 illustrates one exemplary spot pattern which was discovered using the direct ray tracing iterative process of the present invention, where the diagram in FIG. 4 is a simulated pattern created when using a pair of spherical mirrors, with the incoming laser beam making 200 passes between the mirrors. Referring to FIG. 4, both an entrance hole 11 and an exit hole 13 form part of this configuration, resulting in an arrangement which is not reentrant. This type of pattern, including a plurality separate elliptical regions, is quite different from the standard single circular or elliptical patterns associated with the prior art arrangements. In this case, the created pattern includes five separate spot regions I, II, III, IV and V, thus significantly increasing the number of spots (and, as a result, the spot density) formed on the surface of the mirror.

It is also possible to analyze the sensitivity of the final spot position by introducing small perturbations to one or more of the multipass cell parameters during the ray tracing process. This particular process will assist in understanding how the non-reentrant pattern will affect the stability of the output beam position and angle.

Figure 5:
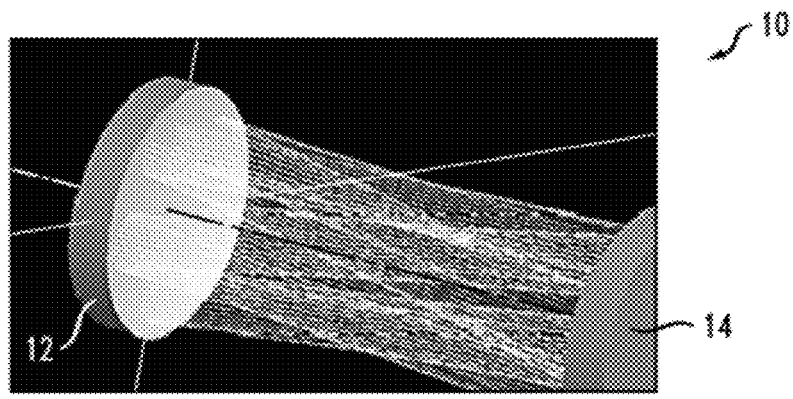
FIG. 5 is a computer-generated ray tracer diagram of the spot pattern of FIG. 4.

FIG. 5 is a commercial ray tracer diagram of the arrangement of FIG. 4, verifying the results as creating these five separate spot regions. FIG. 5 specifically illustrates this implementation in the form of a multipass cell 10 including a first spherical mirror 12 and a second spherical mirror 14. In the past, using reentrant condition-based spherical multipass cells provided a very simple equation (with the paraxial and thin lens approximations) to produce a multipass circular or elliptical configuration. In accordance with the present invention, however, the fact that each individual ray of the input beam experiences a slightly different reflection angle (due to the actual spherical mirror surface) is taken into consideration as each ray is individually traced as it travels within the cell. Such an involved process would be too complicated to use with any expression that allows calculation of the multipass cell design parameters according to a formula (as in the prior art).

Figure 6:
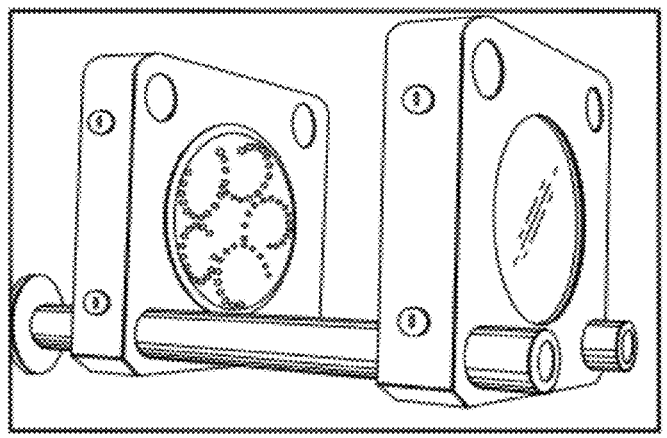
FIG. 6 is a photograph of an actual multipass cell configured on the basis of the parameters associated with the design of FIG. 4.

FIG. 6 is a photograph of a multipass cell formed in accordance with the present invention, illustrating the creation of a spot pattern similar to the arrangement of FIGS. 4 and 5. This particular arrangement has a physical length of approximately 3.51 cm (distance d between mirrors), but creates an optical path length of 3.7 meters (a total of 107 bounces).

These multipass cells as formed in accordance with the present invention are particularly well-suited for applications where the focal length f is small. A small focal length produces a strong curvature of the concave mirrors, providing a relatively large spherical aberration. Heretofore, when using the prior art "thin lens" approximation, this spherical aberration was ignored, allowing for the use of simple design equations, but with no possibility of simulating intricate patterns similar to those described herein.

The parameters of concern for the simulation process of the present invention include the following: (1) minimum spot separation (on each mirror)—that is, the minimum separation without creating an overlap; (2) "within bounds"—a restraint that all rays must "land" on the mirror surface; (3) total optical path length (defined as "final distance"); (4) clearance from any predefined gap in the mirror where rays should not bounce; (5) x,y location of the entrance hole on a mirror for input beam; (6) x,y location of the exit hole on a mirror for the output beam; (7) angle of input beam (with respect to the optical axis of the cell); (8) angle of output beam, (with respect to the optical axis of the cell); (9) distance between mirrors; (10) focal length of the mirrors; and (11) diameter of the mirrors.

In performing the optimization in accordance with the present invention the inputs that are iterated to find an acceptable solution include one or more of the following: (a) the input location of the input beam (x,y) at the first mirror; (2) the angle of the incoming beam (as measured with respect to the optical axis of the system); (3) the distance d between the mirrors; and (4) the number of passes N.

The outputs that are desired to be optimized include the following: (a) minimum spot size; (b) ensuring that all spots are within the bounds of the mirror surface; (c) optical path length; (d) exit location of beam; (e) exit angle; (f) separation between entrance and exit apertures; and (g) location of "last spot" with respect to exit hole (to make sure that there is sufficient space for manufacturing requirements, for example).

Artificial intelligence-based optimization (which can be implemented using a genetic algorithm) is used in the decision making process of developing an acceptable spot pattern in accordance with the present invention, by varying one or more of the identified input parameters to optimize the final design of the multipass cell. Genetic algorithms are general-purpose search algorithms based upon the principles of evolution observed in nature, such as selection, crossover and mutation. The specific "gene" values are usually initialized to random values within defined boundaries. A "chromosome" is made of a collection of genes and is thereafter evaluated by a fitness function to determine the quality of the solution.

Figure 7:
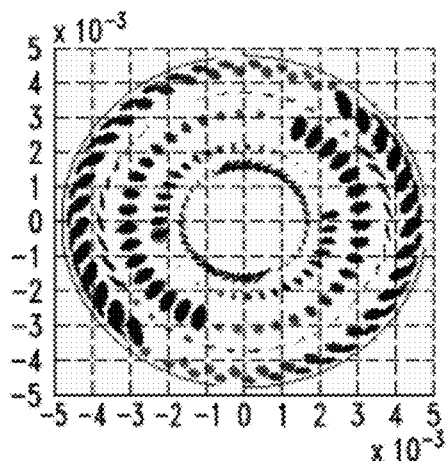
FIG. 7 illustrates another exemplary spot pattern developed using the technique of the present invention, in this case generating 459 passes between mirrors in a multipass cell.
Figure 8:
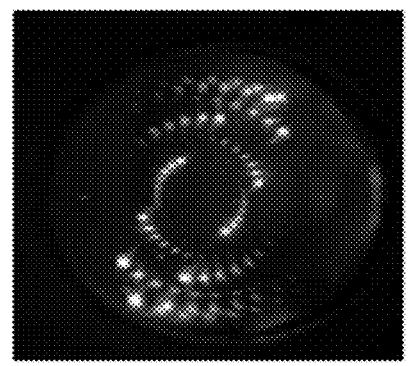
FIG. 8 is a photograph of the embodiment of FIG. 7.
Figure 9:
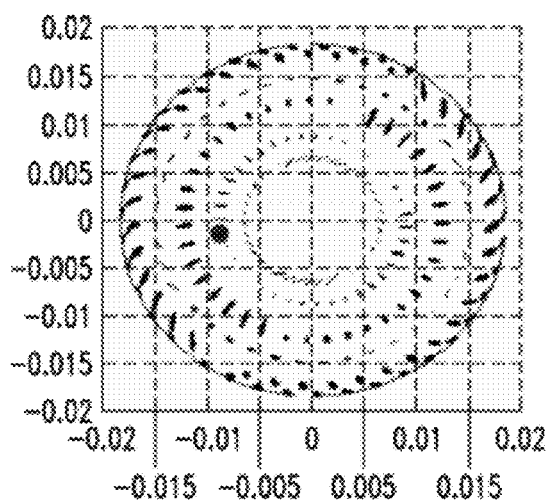
FIG. 9 illustrates a modification of the spot pattern of FIG. 7, created by included a mode matching lens at the input of the multipass cell.

As described above, by varying one or more of the input parameters and using AI-based optimization, a number of very different spot patterns have been identified as creating high density configurations. FIGS. 7 and 8 illustrate a simulated pattern for an exemplary high fill density multipass cell formed using the direct ray tracing and AI optimization procedures of the present invention. In particular, FIG. 7 is a diagram of the simulation results for a multipass cell that includes 459 passes, with a photograph of the associated multipass cell shown in FIG. 8. By adding a mode matching lens to the input of the arrangement, the spot pattern size can be changed, as shown in FIG. 9. This particular embodiment resulted in creating an optical path length of 57.6 meters, using 1.5 inch diameter plano-concave spherical mirrors, spaced a distance of 12.6 cm apart.

Figure 10:
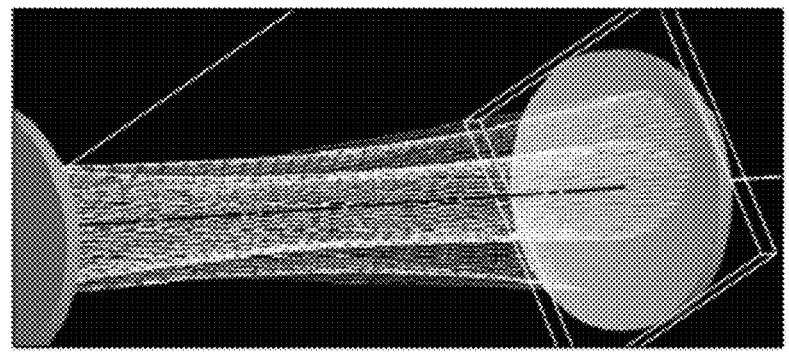
FIG. 10 is a computer-generated ray trace of yet another multipass cell configuration formed in accordance with the present invention, in this case creating a spot pattern that appears as two overlapping "C"'s.

FIG. 10 is a computer-generated ray trace of yet another multipass cell configuration that was formed using the technique of the present invention, where the intricate spot pattern appears as two C's that are overlapped, again creating a dense spot pattern on the mirror surface.

As mentioned above, the direct ray tracing technique of the present invention may also be used with more complicated mirror configurations. For example, an asymmetric cell may be desired, where the focal lengths of the two mirrors are different. The difference in focal length then becomes merely another parameter added to the simulation process of tracing the rays as they bounce between mirrors. That is, the computer tracing algorithm can simply change one mirror's radius of curvature and utilize the same AI-based iterative optimization process to find different cell configuration solutions. Offsets and tilts (and different reflectivities) can similarly be addressed by adjusting the characteristics of the mirror in the computer tracing algorithm. Different input wavelengths and adjustments in the number of rays forming the beam may also be utilized.

Additionally, the techniques of the present invention can be used with multipass cell configurations where the input beam is injected into a cell without a hole. In this instance, therefore, the "hole position" variables are obviously eliminated from the optimization process and replaced by information defining the "injection location" near a mirror. Both cavity-enhanced spectroscopy and integrated cavity output spectroscopy (ICOS) are applications where a beam is injected into a cavity made by mirrors with high reflectively coatings (typically>99%), which allows for many transverse modes to exist within the cavity at once, with the beam not generally reentrant.

Other possible multipass cell configurations that utilize more than two mirrors may also be analyzed with the direct ray tracing iterative optimization technique of the present invention. While any arrangement that utilizes more than a pair of mirrors is more intricate in design and would require the direct tracing of more independent rays, it is possible to extend the teachings of the present invention to discover multipass cell configurations using three or more minors.

A wide variety of optical applications are considered to benefit from the increased interaction lengths that are possible with the high spot density multipass cells formed in accordance with the present invention. For example, the arrangements as described above can be combined with other spectroscopic methods, such as photoacoustic spectroscopy or Faraday rotation spectroscopy (FRS). In photoacoustic spectroscopy, the modulated energy from the absorbed, modulated light produces pressure waves that can be set to audio frequencies and thereafter detected with microphones. In FRS, the amount of polarization rotation along the light beam path is dependent on path length. Therefore, the compact multipass cell design of the present invention allows for the creation of an extremely long path length in a small volume.

In cavity enhanced methods such as off-axis integrated cavity output spectroscopy, the gas cell uses ultra-high reflectivity minors and allows the beam to bounce many more times than standard multipass cells. These cells are typically implemented in a slightly different way, since injection is not done through holes, and the spots typically overlap a great deal to put as many separate spot locations on the minor before each individual ray is reentrant. However, the spot patterns injected into a two spherical mirror off-axis configuration are circular, since these patterns were assumed to be the only patterns for spherical mirror based two-mirror cells. The spot spacing for these off-axis cavities are set to avoid the reentrant solution as much as possible. These cells also benefit from astigmatic spot patterns, but the manufacturing costs are typically too high to provide both accurate astigmatic mirror characteristics and ultra-high reflectivity dielectric coatings, thus most of these types of implementations use simple spherical mirrors. The present invention can provide new patterns for such off-axis cavities using spherical mirrors by spreading the spots over the mirrors, avoiding the reentrant condition for more bounces than the standard circular patterns.

Other modifications of a multipass cell of the present invention include the ability to "switch" the identity of the entrance and exit holes by using optical couplings that can easily modify the direction of the optical path (for example, fiber-based couplings are relatively easy to modify and change port locations). Additional optics may be added in the input signal path (such as the lens, mentioned above) to change the properties of the input beam and, as a result, change the produced spot pattern. Other environmental factors, such as temperature and pressure, can be controlled within the cell using attached sensors and control methods.

It will be apparent to those skilled in the art that various modifications and variations can be made in the system and method of the present invention without departing from the spirit or scope of the invention. Thus, it is intended that the present invention cover the modification and variations of this invention, provided they come within the scope of the appended claims and their equivalents.

What is claimed is:

1. A multipass optical cell comprising
   a first mirror element forming a first end termination of the multipass optical cell; and
   at least a second mirror element forming a second end termination of the multipass optical cell, the second mirror element disposed with respect to the first mirror element so that an incoming light beam injected into the multipass optical cell will reflect multiple times between the first mirror element and the second mirror element, creating a spot pattern of locations where the beam impinges the reflecting surface of the first and second mirror elements, wherein one or more cell parameters are configured using optimization via direct, three-dimensional ray tracing of a plurality of separate rays forming the incoming light beam, utilizing actual curvature values taking into account non-paraxial properties including spherical aberration of the first and second mirror elements to create an intricate, dense spot pattern.

2. A multipass optical cell as defined in claim 1 wherein the cell parameters are selected from the group consisting of: the orientation of the incoming beam with respect to an optical axis of the first mirror element, the separation distance between the first mirror element and the second mirror element, and the location of an exit hole on either one of the first and second mirror elements.

3. A multipass optical cell as defined in claim 1 wherein the incoming light beam is injected through an entrance hole formed in the first mirror element and the optimized cell parameters further include the location of the entrance hole on the first mirror element.

4. A multipass optical cell as defined in claim 3 wherein the curvature of the first mirror element is different from the curvature of the second mirror element, forming an asymmetric multipass optical cell.

5. A multipass optical cell as defined in claim 3 wherein the configuration of the elements is optimized to create a dense spot pattern defining a larger number of passes than utilized with a re-entrant spherical mirror multipass optical cell.

6. A multipass optical cell as defined in claim 3 where additional cell parameters analyzed to create a configuration include a minimum separation between the entrance hole and an exit hole formed in a mirror element, a minimum spacing between a spot and the exit hole, and a mirror clear aperture.

7. A multipass optical cell as defined in claim 1 wherein the first and second mirror elements comprise concave spherical elements.

8. A multipass optical cell as defined in claim 7 wherein the curvature of the first mirror element is essentially the same as the curvature of the second mirror element, forming a symmetric multipass optical cell.

9. A multipass optical cell as defined in claim 1 wherein the first and second mirror elements comprise astigmatic mirror elements.

10. A multipass optical cell as defined in claim 1 wherein at least one mirror element comprises a cylindrical mirror element.

11. A multipass optical cell as defined in claim 1 wherein the first mirror element comprises a split-spherical mirror element.

12. A multipass optical cell as defined in claim 1 wherein the at least one second mirror element comprises a plurality of mirror elements, aligned with the first mirror element to form a multipass cell where the light beam is reflected off of each mirror element as it travels within the cell.

13. A multipass optical cell as defined in claim 1 wherein the cell parameters are modified using an iterative artificial intelligence-based optimization process to discover an intricate spot pattern.

14. A multipass optical cell as defined in claim 13 wherein the artificial intelligence-based optimization process utilizes a genetic algorithm optimization process to discover the intricate spot pattern.

15. A multipass optical cell as defined in claim 1 wherein the multipass optical cell further comprises an optical coupling arrangement for injecting an input beam into, and extracting an output beam from, the multipass optical cell.

16. A multipass optical cell as defined in claim 15 wherein the optical coupling arrangement comprises an optical fiber-based coupling arrangement.

17. A multipass optical cell as defined in claim 15 wherein the coupling arrangement is coupled to both terminations of the cell, providing for an input beam to be injected at either termination.

18. A multipass optical cell as defined in claim 17 wherein the arrangement further includes a switch for changing the injection location of an input beam.

19. A multipass optical cell as defined in claim 1, wherein the multipass optical cell is utilized in an application selected from the group consisting of: gas-filled absorption cells, photoacoustic spectroscopy, Faraday rotation spectroscopy, cavity-enhanced spectroscopy, off-axis integrated cavity output spectroscopy and laser gain medium.

20. A method of creating a dense spot pattern within a multipass optical cell, the method including the steps of:
   a) positioning a first mirror element as a first end termination of the multipass optical cell, the first mirror element having a first, defined curvature,
   b) positioning a second mirror element as a second end termination of the multipass optical cell, the second mirror element having a second, defined curvature, wherein the first and second mirror elements are separated by a distance d;
   c) defining an input beam as a plurality of separate three-dimensional rays;
   d) directly tracing the reflections of each separate ray as it interacts with the first and second mirror elements as a function of the actual curvatures of the first and second mirror elements, taking into account non-paraxial properties including spherical aberration; and
   e) using artificial intelligence optimization to simulate varying one or more of: the location of the entrance hole on the first mirror element, the orientation of the incoming beam with respect to an optical axis of the first mirror element, the separation distance between the first mirror element and the second mirror element, and the location of an exit hole on either one of the first and second mirror elements to create a dense spot pattern.

21. The method of claim 20, wherein step e) further includes optimization of one or more of the following: minimum spot size, mirror clear aperture, optical path length, exit location of beam, exit angle, separation between entrance and exit holes, location of spots with respect to exit hole.

22. The method of claim 20, wherein in performing steps a) and b), spherical mirrors are provided.

23. The method of claim 22 wherein in performing step e), the optimization creates a configuration with a spot pattern denser than that associated with a re-entrant spherical mirror multipass optical cell.

24. The method of claim 20 wherein in performing step e), a genetic algorithm is used in the optimization process.

25. The method of claim 20 wherein in performing step e), a parameter associated with shaping an incoming beam is optimized to create an output beam of a predetermined shape.

26. The method of claim 25 where the output beam is preferably a spherical shape and the optimization is performed to determine an input beam shape suitable to create a spherical output beam.

* * * * *